United States Patent
Abousleiman

(12) 
(10) Patent No.: US 8,628,503 B1
(45) Date of Patent: Jan. 14, 2014

(54) APPARATUS AND A METHOD FOR HANDS FREE TREATMENT OF DRY AND/OR DISCOMFORTED EYES

(76) Inventor: Rami Abousleiman, Auburn Hills, MI (US)

( * ) Notice: Subject to any disclaimer, the term of this patent is extended or adjusted under 35 U.S.C. 154(b) by 0 days.

(21) Appl. No.: 13/507,474

(22) Filed: Jul. 2, 2012

(51) Int. Cl.
*A61H 1/00* (2006.01)

(52) U.S. Cl.
USPC ........................ 604/290; 604/890.1

(58) Field of Classification Search
None
See application file for complete search history.

(56) References Cited

U.S. PATENT DOCUMENTS

| 5,346,132 | A | 9/1994 | Hahn et al. |
| 6,251,952 | B1 | 6/2001 | Siff |
| 6,297,289 | B2 | 10/2001 | Siff |
| 2011/0184387 | A1* | 7/2011 | Hyde et al. ................. 604/890.1 |

* cited by examiner

*Primary Examiner* — Leslie Deak
*Assistant Examiner* — Sara Sass
(74) *Attorney, Agent, or Firm* — John G. Chupa

(57) ABSTRACT

An eye watering/treating hands free system 12 for use with a computer system 10 or any other type of system and which selectively emits an eye watering/treating substance 80 in the direction of the eyes 35, 37 of a user 30 in order to treat eyes 35, 37 for dryness and/or discomfort.

1 Claim, 2 Drawing Sheets

APPARATUS AND A METHOD FOR HANDS FREE TREATMENT OF DRY AND/OR DISCOMFORTED EYES

FIELD OF THE INVENTION

The present invention generally relates to a hands free apparatus and to a hands free method for treating dry and/or discomforted eyes and more particularly, to an apparatus and a method that neither requires nor excludes user input for treating dry eyes and/or discomfort of the eyes of a user of some apparatus or system, such as by way of example and without limitation, a computer system.

BACKGROUND OF THE INVENTION

It is known that long term use of a computer or other apparatus may cause a user's eyes to become dry and/or discomforted due to a lack of tear production caused by a continued gazing into a computer monitor or some other type of apparatus, or by constant strain of the eye focusing at the same distance for a prolonged period of time. Over time, it is thought that this "dry eye" condition may detrimentally affect one's eyesight. Traditionally, to alleviate this condition, computer users (and users of other types of apparatuses requiring a constant "gazing" into an area, such as users of some types of production machinery or truck drivers) take frequent breaks from their work, thereby "resting" their eyes. While such rest does temporarily alleviate the foregoing difficulties, it has a disadvantage of decreasing productively and increasing cost. Users also tend to manually apply eye drops that will insert a moisturizing liquid in the eyes. However, when such preventive measures are not taken, permanent damage to the eyes may occur.

There is therefore a need for, and it is a non-limiting object of this invention to provide, an "in process" methodology and apparatus which waters/treats the eyes of those gazing upon a computer screen or performing some other type of work, without requiring an interruption in the overall work flow, work process, or any other type of activities including leisure and which may be accomplished in a hands-free manner.

SUMMARY OF THE INVENTION

It is a first non-limiting object of the present invention to provide a method and an apparatus which overcomes the various disadvantages of the prior afore-described "dry eye" alleviation strategies.

It is a second non-limiting object of the present invention to provide a method and an apparatus which waters/treats the eyes of computer users and users of other systems without appreciably reducing productivity and increasing overall production cost.

It is a third non-limiting object of the present invention to provide a method and an apparatus which selectively waters/treats the eyes of users in an "in process" manner and in a hands-free manner.

According to a first non-limiting aspect of the present invention, an apparatus for selectively watering/treating eyes is provided. Particularly, the apparatus includes a first system monitoring portion which selectively generates a signal; and a second portion which is coupled to the first system monitoring portion and which selectively emits an eye watering/treating agent in response to the generated signal.

According to a second non-limiting aspect of the present invention, a computer system is provided and includes a processor portion which selectively generates a signal; and a second portion which is coupled to the processor portion and which selectively emits an eye watering/treating agent in response to the generated signal.

According to a third non-limiting aspect of the present invention, a method for selectively watering/treating the eyes of a user of an apparatus is provided. Particularly, the method includes the steps of monitoring the use of said apparatus; determining if the apparatus has been used for a certain amount of time; and emitting an eye watering/treating agent only if the apparatus has been used for the certain amount of time, thereby watering/treating the eyes of the user of the apparatus.

These and other features, aspects, and advantages of the present invention will become apparent from a reading of the following detailed description of the preferred embodiment of the inventions, including the subjoined claims, and by reference to the following drawings.

DETAILED DESCRIPTION OF THE PREFERRED EMBODIMENT OF THE INVENTIONS

Figure 1:
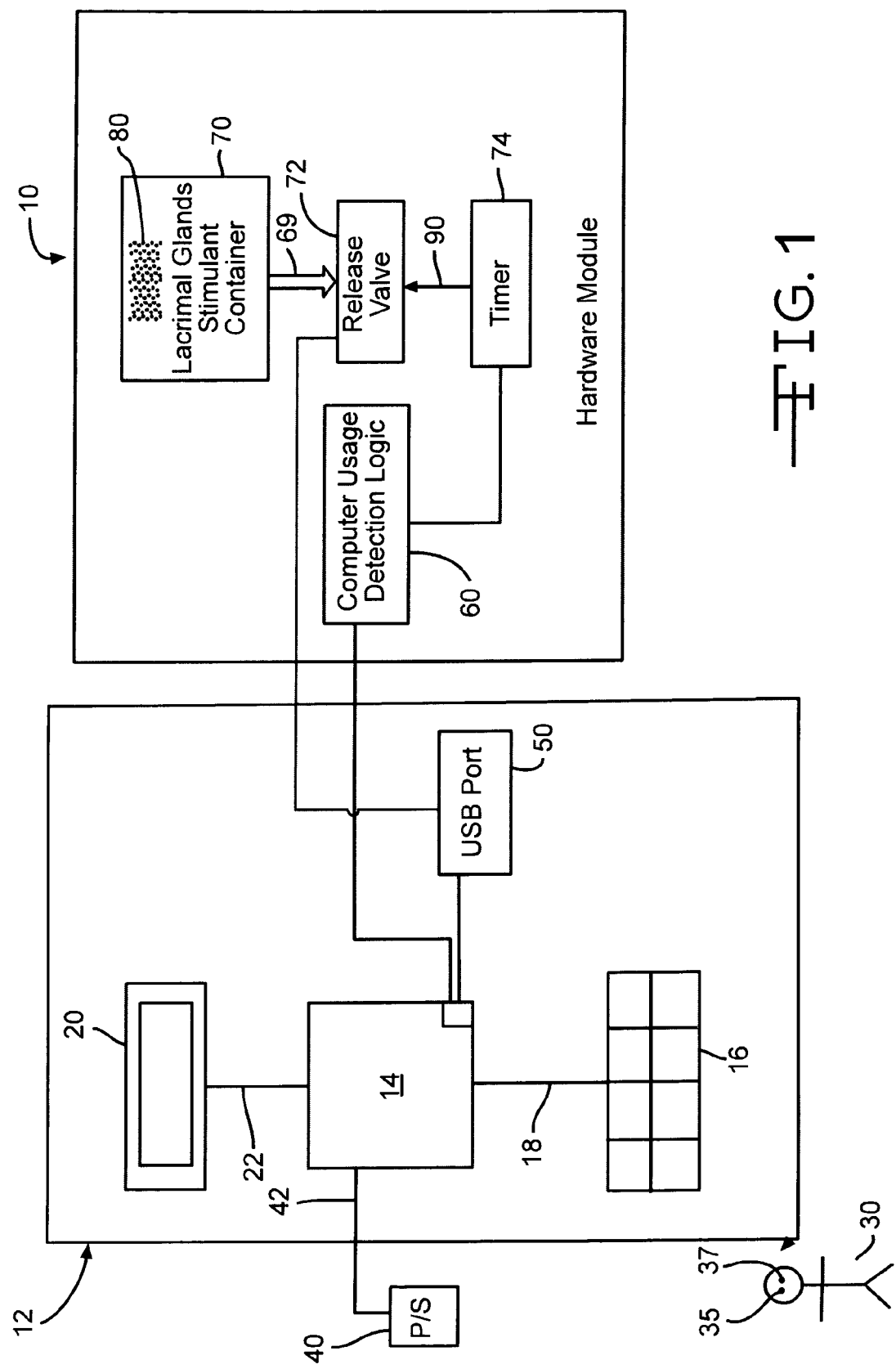
FIG. 1 is a block diagram of the eye watering/treating apparatus which is made in accordance with the teachings of the preferred embodiment of the inventions, in combination with a computer assembly.

Referring now to FIG. 1, there is shown an eye watering system 10 which is made in accordance with the teachings of the preferred embodiment of the invention, in combination with a computer system or apparatus 12.

Particularly, in one non-limiting example, the computer system 12 includes a processor portion 14 which may include a commercially available "I3" type processor which is available from the Intel® Corporation, although other types of processors may be utilized. Further, the computer system 12 includes a keyboard 16 which is coupled to the processor portion 14 by the bus 18, and a monitor or display portion 20 which is coupled to the processor portion 14 by the bus 22. It should be appreciated that the monitor or display 20 is used, by the processor portion 14, to display information to a user, such as user 30, and it is the continual use of the monitor or display 20, by the user 30 that dries out the user's eyes 35, 37. Further, the processor portion 14 is coupled to a source of electrical power 40 by the bus 42 and the power supply 40 provides operational electrical energy to the processor portion 14. Power supply 40 could comprise a battery. The information appearing upon the display 20 may be created by the user 30 by use of keyboard 16 or any other device, and communicated to display 20 by use of processor 14 and bus 22. System 12 is meant to generally represent a computer system which is commercially available.

The computer system or apparatus 12 further includes one or more USB type ports (but not limited to) 50 which allow external systems, apparatuses, and/or objects to communicate with the processor portion 14 and through which electrical power may be communicated from the source of electrical energy 40 to that which is externally coupled to the port 50 (i.e., "externally coupled" means that which is coupled to the port 50 and which is external from the processor portion 14).

As further shown, the eye watering system 10 includes a computer usage detection circuit assembly 60, which is coupled to the processor portion 14, and which detects the usage of the computer system 10. For example, the assembly 60 may comprise, in one non-limiting example, a simple single pole single throw commercially available switch that the user 30 activates or "switches" when beginning to use the computer system 12 and de-activates when computer use is done. In this manual example, the computer user 30 selectively activates and deactivates the detection circuit 60. In yet another non-limiting embodiment, the detection circuitry 60 comprises a commercially available "MAX 6808", "MAX 6807", and/or "MAX 6806" low cost voltage detection circuit which is available from Maxim Integrated Products of San Jose, Calif. The voltage detection circuit will then detect when voltage is applied to the monitor 20, or the voltage detection circuit will detect when voltage is applied to the processor portion 14 from the power supply 40. Such voltage is then communicated from the processor portion 14 to the monitor 20, by means of bus 20, in order to allow the monitor 20 to become operable. In the manual mode of such operation, the switch 60 may be activated and then deactivated each time the user 30 has eye discomfort.

The eye watering system 10 further includes a container 70 of a lacrimal glands stimulant gas/vaporized liquid which, in one non-limiting embodiment, comprises propanethial-S-oxide, but other stimulants may be utilized. The system 10 further includes a release valve 72 which is physically and communicatively coupled to the canister 70, and a valve control circuit 74 which is physically coupled to the valve 72. In operation, as will be discussed shortly, the eye watering material 80, which is contained within the canister 70, is communicated to the valve 72. The valve 72 is coupled to the port 50 and selectively receives operational electrical energy which emanates from the port 50. The valve control circuit 74 is coupled to the detection circuit 60 and becomes activated when the detection circuit 60 senses voltage is present at or to the monitor or display 20 or to the processor portion 14, or, in an alternate embodiment, when forced to be active by the user 30 (when no voltage detection occurs).

In one non-limiting embodiment, the valve 72 comprises a solenoid valve and the portion 74 comprises a commercially available Burkert Timer Unit which is obtainable from The Valve Shop.Com. Other types of timer circuits and control valves may be used. The timer portion 74 then controls the periods of discharge of the contained material 80 by periodically generating a signal to the valve 72, by use of bus 90, which causes the valve 72, only if it is first activated by receiving electrical power from the portion 60, to discharge some of the material 80 in the direction of the user 30. That is, the valve 72, in the most preferred embodiment of the invention, is intentionally placed in close proximity to the user 30.

Figure 2:
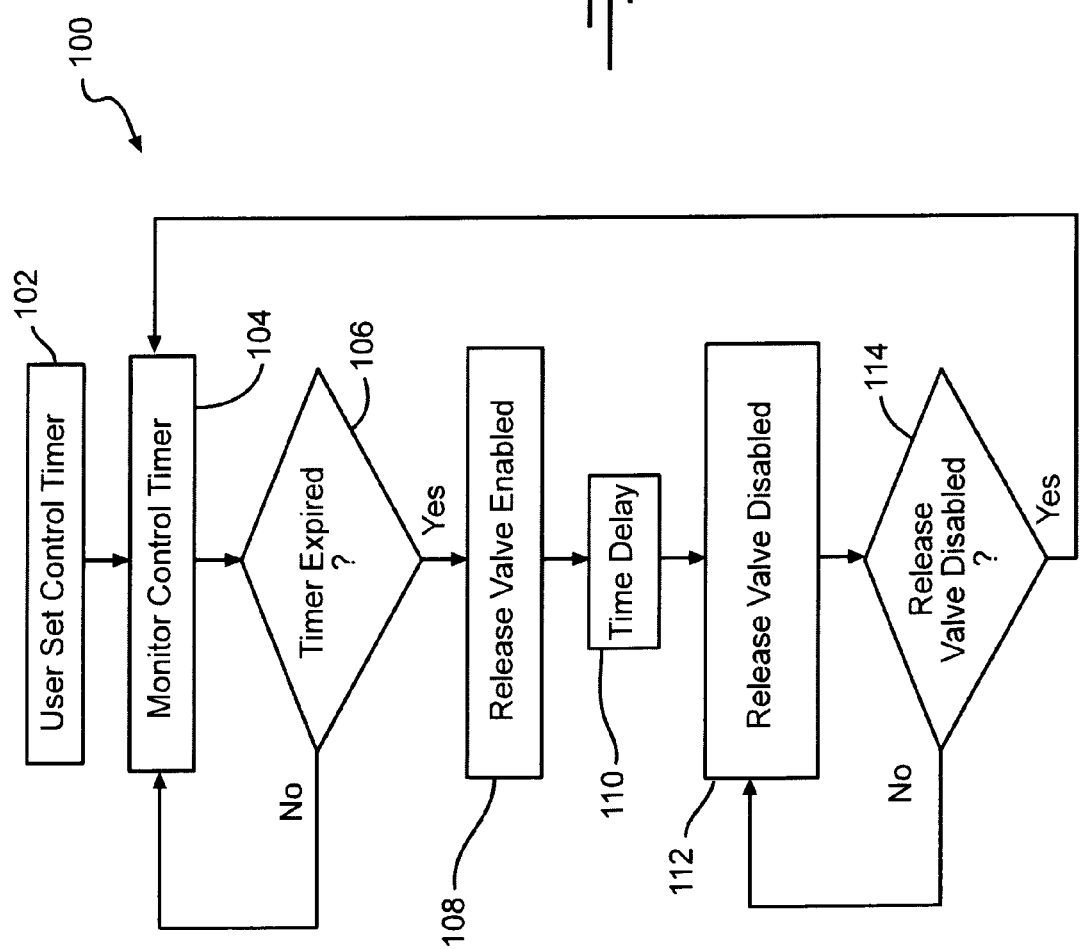
FIG. 2 is a flow chart of a sequence of steps which cooperatively form a methodology of the preferred embodiment of the inventions.

Referring now to FIG. 2, there is a flow chart 100 which illustrates the sequence of steps associated with the methodology of the preferred embodiment of the invention. Particularly, the methodology 100 includes an initial step 102 in which the periodic times for material generation is set or programmed by the user 30. This occurs by programming the timer or activating the switch in the manual embodiment. Step 102 is followed by step 104 in which the portion 74 continues to monitor whether the time for material emanation has arrived. If the switch is activated, in the manual mode, the time for material emanation is always active. Step 104 is followed by step 106 in which the portion 74 determines whether the period for material emanation has arrived or whether the switch (in the manual embodiment) is activated. If the period has arrived, then step 106 is followed by step 108. Alternatively, step 106 is followed by step 104.

In step 108 the portion 74 generates an enabling signal to the valve 72 by use of the bus 90, thereby causing some of the material 80 to be discharged. Step 110 follows step 108 and, in this step 110, the signal is maintained in order to ensure that enough time has passed for some of the material 80 to physically travel to and through the valve. This time period may be programmed into the portion 74. Step 112 follows step 110 and, in this step 112, the valve 72 is disabled by discontinuing the transmission and communication of the signal 90. Step 114 follows step 112 and in this step 114 the portion 74 determines whether it has stopped generating and transmitting the signal 90. If it has not, then step 114 is followed by step 112. Alternatively, step 114 is followed by step 104. At any time, the user 30 may adjust or change the period of time used by the portion 74 to cause the material 80 to be selectively emitted by adjusting the setting on the timer or by manually deactivating the switch (in the manual mode). If the switch is left activated, in the manual mode, then the material so will be emitted continually.

The inventions are not limited to their exact construction or embodiments which have been delineated above, but that various changes and modifications may be made to them without departing from the spirit and the scope of the inventions as they are more fully delineated in the following claims. It should be appreciated that eye watering system 10 keeps the eyes 35, 37 of a user 30 moist (ultimately making user 30 more comfortable) and that the user 30 may be using a computer system 12 or any other type of system requiring the user 30 to gaze into a screen or other area for an extended period of time. Further, it should be appreciated, that the methodology 100 represents an "in process" methodology which does not require the overall process (such as the use of a computer system 12) to be interrupted or to change, thereby not detrimentally effecting productivity. The process is also "hands free" because the user 30 does not need to interrupt his or her work flow to cause the material 80 to be desirably emitted.

What is claimed is:

1. A method for an individual to operate a computer comprising the steps of providing a computer which comprises a processor which is operable under stored program control and which selectively receives a first voltage signal; a keyboard which is coupled to said processor; a monitor which is coupled to said processor, wherein said monitor selectively receives a second voltage signal, which receives information from said processor, and which displays said received information; a container of lacrimal gland stimulant; a voltage detection circuit which is coupled to said processor and which detects the occurrence of at least one of said first and second voltage signals; a solenoid valve which is coupled to said container of said lacrimal gland stimulant and to said processor; a timer which is coupled to said voltage detection circuit and to said container of said solenoid valve and wherein said timer comprises a programmable timer in which a plurality of distinct time periods may be selectively programmable and specified; and wherein said method further comprises the steps of programming said timer effective to specify only a single pre-defined time period; placing said solenoid valve in close proximity to the eyes of said user; causing said first voltage signal to be received by said processor; causing said second voltage signal to be received by said monitor; detecting, by use of said voltage detection circuit, one of said first and said second voltage signals; causing said voltage detection circuit to generate a signal to said solenoid valve only if at least one of said first and said second voltage signals have been detected, thereby causing said valve to cause some of said contained lacrimal stimulant material to be emitted from said container towards the eyes of said user without interrupting the use of said computer system by said user, thereby moisturizing the eyes of said user; wherein said lacrimal stimulant material is emitted only during intermittent periods of time which are each equal to said single-defined time period, and wherein said emission of said lacrimal stimulant material ceases when detection of said at least one voltage signal ceases and wherein said method further comprises the steps of selecting a second time period and causing said voltage detection circuit to generate a third signal to said solenoid valve, thereby causing said solenoid valve to cause some of said contained lacrimal stimulant material to be intermittently emitted from said container toward the eyes of said user without interrupting the use of the computer system by said user and only during intermittent periods of time which are each equal to said second time period and wherein said method of further comprising the step of allowing the user to force said emission of said lacrimal stimulant material at any time desired by the user and during the operation of the computer system by the user.

\* \* \* \* \*